US00PP14601P29

(12) United States Plant Patent
Eijkenboom

(10) Patent No.: US PP14,601 P2
(45) Date of Patent: Mar. 16, 2004

(54) CLERODENDRUM PLANT NAMED 'PINK DIAMOND'

(50) Latin Name: *Clerodendrum bungei*
Varietal Denomination: Pink Diamond

(75) Inventor: John F. H. Eijkenboom, Kaulille Gem. Bocholt (BE)

(73) Assignee: Novitas Plantae, Lisse (NL)

( * ) Notice: Subject to any disclaimer, the term of this patent is extended or adjusted under 35 U.S.C. 154(b) by 16 days.

(21) Appl. No.: 10/437,942

(22) Filed: May 13, 2003

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database 2003/04, GTI Jouve Retrieval Software, Citation for 'Pink Diamond'.*

* cited by examiner

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of Clerodendrum plant named 'Pink Diamond', characterized by its relatively compact, upright and outwardly spreading plant growth habit; green and creamy white variegated leaves; freely flowering habit; relatively long flowering period; and fragrant red purple-colored flowers.

1 Drawing Sheet

Botanical classification/cultivar designation: *Clerodendrum bungei* cultivar Pink Diamond.

BACKGROUND OF THE INVENTION

The present Invention relates to a new and distinct cultivar of Clerodendrum plant, botanically known as *Clerodendrum bungei*, and hereinafter referred to by the name 'Pink Diamond'.

The new Clerodendrum is a naturally-occurring branch mutation of an unidentified selection of *Clerodendrum bungei*, not patented. The new Clerodendrum was discovered by the Inventor in a controlled environment in Sittard, The Netherlands, within a population of plants of the unidentified selection in June, 1994. The new Clerodendrum was selected on the basis of its variegated foliage.

Asexual reproduction of the new cultivar by vegetative cuttings taken in a controlled environment at Sittard, The Netherlands since 1994, has shown that the unique features of this new Clerodendrum are stable and reproduced true to type in successive generations.

SUMMARY OF THE INVENTION

Plants of the cultivar Pink Diamond have not been observed under all possible environmental conditions. The phenotype may vary somewhat with variations in environment such as temperature and light intensity without, however, any variance in genotype.

The following traits have been repeatedly observed and are determined to be the unique characteristics of 'Pink Diamond'. These characteristics in combination distinguish 'Pink Diamond' as a new and distinct cultivar:

1. Relatively compact, upright and outwardly spreading plant growth habit.
2. Green and creamy white variegated leaves.
3. Freely flowering habit.
4. Relatively long flowering period.
5. Fragrant red purple-colored flowers.

Plants of the new Clerodendrum are most similar to plants of the parent selection. In side-by-side comparisons conducted in Sittard, The Netherlands, plants of the new Clerodendrum differed from plants of the parent selection in the following characteristics:

1. Plants of the new Clerodendrum were more compact and slower growing than plants of the parent selection.
2. Plants of the new Clerodendrum had variegated foliage whereas plants of the parent selection had solid green-colored foliage.
3. Flowers of plants of the new Clerodendrum were more fragrant than flowers of plants of the parent selection.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Clerodendrum.

The photograph at the top of the sheet comprises a side perspective view of a typical flowering plant of 'Pink Diamond' grown in a container.

The photograph at the bottom of the sheet is a close-up view of typical flowers and leaves of 'Pink Diamond'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and for the following description were grown for about two years under outdoor field conditions which closely approximate commercial production conditions in Boskoop, The Netherlands. During the production of the plants, day temperatures ranged from 14 to 27° C. and night temperatures ranged from 7 to 14° C. The photographs and description were taken in September, 2001.

Botanical classification: *Clerodendrum bungei* cultivar Pink Diamond.

Parentage: Naturally-occurring branch mutation of an unidentified selection of *Clerodendrum bungei*, not patented.

Propagation:

*Type.*—Vegetative cuttings.

*Time to initiate roots.*—Summer: About 35 days at 20° C. Winter: About 42 days at 15° C.

*Time to produce a rooted cutting.*—Summer: About 42 days at 20° C. Winter: About 70 days at 15° C.

*Root description.*—Fleshy; white in color.

Plant description:

*Form.*—Perennial subshrub; relatively compact, upright and outwardly spreading plant growth habit; broad inverted triangle.

*Plant height.*—About 70 cm.

*Plant diameter.*—About 70 cm.

*Vigor.*—Moderately vigorous.

*Branching habit.*—Basal branching; about three stems develop per plant during the flowering season; pinching enhances branching.

*Flowering stems.*—Length: About 64 cm. Diameter: About 6 mm. Internode length: About 7 cm. Texture: Rough; pubescent. Lenticels: Amount: Abundant. Length: About 4 mm. Diameter: About 1 mm. Color, young stems: 155D. Color, mature stems: 164A to 165A to 165B. Strength: Strong. Color: 141A to 139A.

*Foliage description.*—Arrangement: Opposite, simple. Length: About 13 cm. Width: About 11.5 cm. Shape: Broadly ovate to deltoid. Apex: Abruptly acute. Base: Attenuate. Margin: Irregularly serrate. Texture, upper surface: Sparsely pubescent; rugose. Texture, lower surface: Pubescence at veins; rugose. Venation pattern: Pinnate. Fragrance: When rubbed, heavy musk; unpleasant. Color: Developing foliage, upper surface: 137B to 137C with random spots, 191B; irregular margins, between 150D and 160C. Developing foliage, lower surface: 138B; irregular margins, between 150D and 160C. Fully expanded foliage, upper surface: 189A with random spots, 191B to 191C; irregular margins, between 150D and 155C. Fully expanded foliage, lower surface: 191A to 191B; irregular margins, 150D. Venation, upper and lower surfaces: 144A. Petiole: Length: About 8 cm. Diameter: About 4 mm. Texture, upper and lower surfaces: Smooth, glabrous. Color: 144A; towards the leaf, N186C. Color, lower surface: 138B.

Flower description:

*Flower type and habit.*—Single salverform flowers arranged on compound terminal cymes. Flowers face upright and outwardly. Flowers not persistent.

*Natural flowering season.*—flowering continuous during the late summer, August and September, in The Netherlands; relatively long flowering period.

*Quantity.*—Freely flowering with about 350 flowers and flower buds per compound cyme.

*Fragrance.*—Moderate; sweet, pleasant.

*Flower longevity on the plant.*—About five days.

*Flower buds.*—Length: About 2.6 cm. Diameter: About 4 mm. Shape: Spatulate. Color: 60A to 60B.

*Inflorescence height.*—About 6 cm.

*Inflorescence diameter.*—About 12 cm.

*Flower diameter.*—About 1.9 cm.

*Flower height* (*depth*).—About 2.6 cm.

*Petals.*—Quantity/arrangement: Five or six petals fused at base; free, rotate. Length: About 2.5 cm. Width: About 4 mm. Shape: Spatulate to obovate. Apex: Obtuse. Margin: Entire. Texture, upper and lower surfaces: Smooth, glabrous. Color: When opening, upper surface: 71D. When opening, lower surface: 61B. Fully opened, upper surface: 71D. Fully opened, lower surface: 61C to 71C.

*Sepals.*—Quantity/arrangement: Five sepals fused at base; rotate, calyx campanulate. Length: About 3 mm. Diameter: About 1.5 mm. Shape: Ovate. Apex: Acute. Margin: Entire. Texture, upper and lower surfaces: Pubescent. Color: Immature, upper surface: 53C to 53D. Immature, lower surface: 145C to 145D; towards the margins, 53C. Mature, upper surface: 145B; towards the margins, 53D. Mature, lower surface: 145C to 145D; towards the margins, 53C.

*Peduncles.*—Length: About 4 cm. Diameter: About 2.5 mm. Angle: About 30 to 45° from vertical. Strength: Strong. Texture: Pubescent. Color: 141A to 139A.

*Pedicels.*—Length: About 3 mm. Diameter: About 1 mm. Angle: Upright to about 60° from stem. Strength: Moderately strong. Texture: Pubescent. Color: 144A.

*Reproductive structures.*—Androecium: Stamen quantity per plant: About four. Anther length: About 2 mm. Anther shape: Reniform. Anther color: 176A to 176B. Pollen amount: Scarce. Pollen color: Whitish. Gynoecium: Pistil quantity per flower: Typically one. Pistil length: About 2.4 mm. Stigma shape: Pointed. Stigma color: 175A. Style length: About 2.4 mm. Style color: N155A. Ovary color: 145B to 145C.

*Seeds/fruits.*—Seed and fruit development has not been observed.

Disease/pest resistance: Resistance to pathogens or pests common to Clerodendrum has not been observed.

Temperature tolerance: Plants of the new Clerodendrum have been observed to be tolerant to temperatures from about −5 to 40° C.

It is claimed:

1. A new and distinct cultivar of Clerodendrum plant named 'Pink Diamond', as illustrated and described.

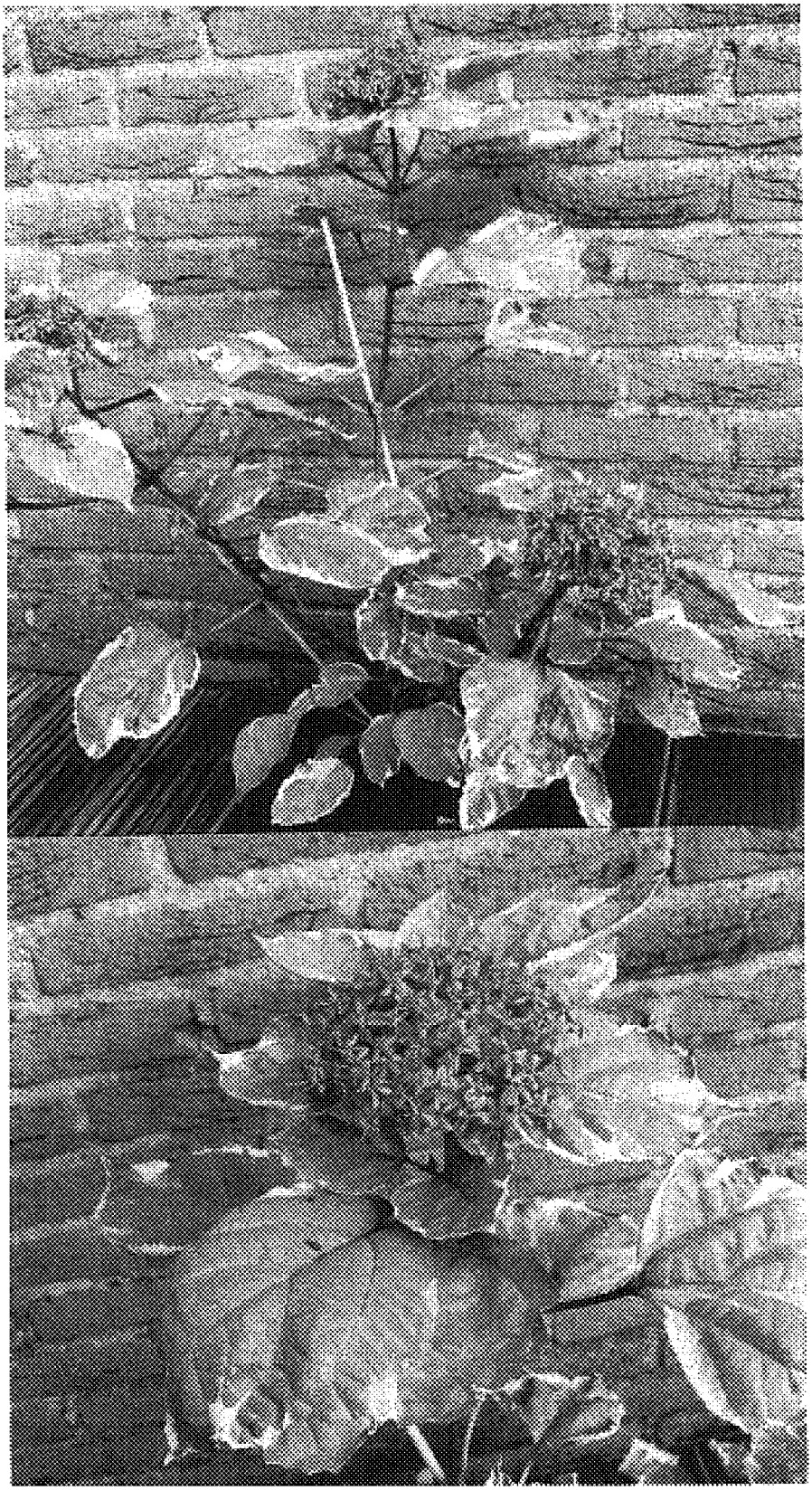

* * * * *